(12) United States Patent
Schön

(10) Patent No.: US 6,911,185 B1
(45) Date of Patent: Jun. 28, 2005

(54) FLUIDIZED-BED REACTOR FOR THE OXYCHLORINATION OF ETHYENE, OXYGEN AND HCL

(75) Inventor: Harmut Schön, Oberusel (DE)

(73) Assignee: Krupp Unde GmbH, Dortmund (DE)

(*) Notice: Subject to any disclaimer, the term of this patent is extended or adjusted under 35 U.S.C. 154(b) by 0 days.

(21) Appl. No.: 09/415,673

(22) Filed: Oct. 12, 1999

(30) Foreign Application Priority Data

Oct. 28, 1998 (DE) .......................... 198 49 709

(51) Int. Cl.[7] .......................... B01J 8/24; F28D 13/00; C07C 17/156; F28F 9/00
(52) U.S. Cl. .................... 422/146; 422/139; 422/198; 422/200; 422/202; 422/203; 165/104.16; 165/176; 570/243; 570/224
(58) Field of Search .................. 570/243, 224; 165/DIG. 481, DIG. 482, DIG. 483, DIG. 484, DIG. 488, DIG. 489, DIG. 471, 104.16, 176, 143; 422/139, 146, 140, 141, 147, 198, 142–145, 188–190, 200–203, 211; 122/511, 235.15; 560/243, 224; 34/578

(56) References Cited

U.S. PATENT DOCUMENTS

| | | | | |
|---|---|---|---|---|
| 1,598,062 A | * | 8/1926 | Dienner et al. | 122/221 |
| 1,848,801 A | * | 3/1932 | Pettibone et al. | 122/235.15 |
| 2,099,186 A | * | 11/1937 | Anderegg | 165/110 |
| 2,391,244 A | * | 12/1945 | Jackson | 165/159 |
| 2,931,711 A | * | 4/1960 | Walker | 122/4 D |
| 3,196,943 A | * | 7/1965 | Haerter | 165/174 |
| 3,679,373 A | * | 7/1972 | Vancamp | 422/146 |
| 3,833,051 A | * | 9/1974 | Frank | 110/342 |
| 3,991,096 A | * | 11/1976 | Bortolini et al. | 558/320 |
| 4,117,885 A | * | 10/1978 | Nickerson et al. | 122/365 |
| 4,368,173 A | | 1/1983 | Jimenez et al. | 422/197 |
| 4,553,502 A | * | 11/1985 | Dreuilhe et al. | 122/4 D |
| 4,593,755 A | * | 6/1986 | Rogers, Jr. | 165/145 |
| 4,811,696 A | * | 3/1989 | Lacquement et al. | 122/235.15 |
| 5,088,294 A | * | 2/1992 | Ando | 62/119 |
| 5,123,480 A | * | 6/1992 | Dixit | 165/104.16 |
| 5,700,432 A | * | 12/1997 | Tanaka et al. | 422/146 |

FOREIGN PATENT DOCUMENTS

| | | |
|---|---|---|
| DE | 2628177 | 6/1976 |
| DE | 4131446 | 9/1991 |
| DE | 4305001 | 2/1993 |

OTHER PUBLICATIONS

PCT International Patent No.: WO 96/26003 dated Aug. 29, 1996.

* cited by examiner

*Primary Examiner*—Hien Tran
*Assistant Examiner*—Jennifer Leung
(74) *Attorney, Agent, or Firm*—Katten Muchin Zavis Rosenman

(57) ABSTRACT

A fluidized-bed reactor for the oxychlorination of ethylene, oxygen and HCL, comprises a heat exchanger, having tube packets in the fluidized-bed for releasing the heat evolved from exothermic reaction to a heat-transfer medium in the tube packets, in particular to water/steam. The tube packets come into contact with water via a ring pipe and the steam being removed via a ring pipe to provide an economical solution with which expensive drilled passages are avoided, the calculation for ring pipes is facilitated and a large number of wall passages is dispensed with. This is achieved by the ring pipe being mounted as a collector or chamber directly on the reactor wall.

11 Claims, 2 Drawing Sheets

FLUIDIZED-BED REACTOR FOR THE OXYCHLORINATION OF ETHYENE, OXYGEN AND HCL

Figure 1:
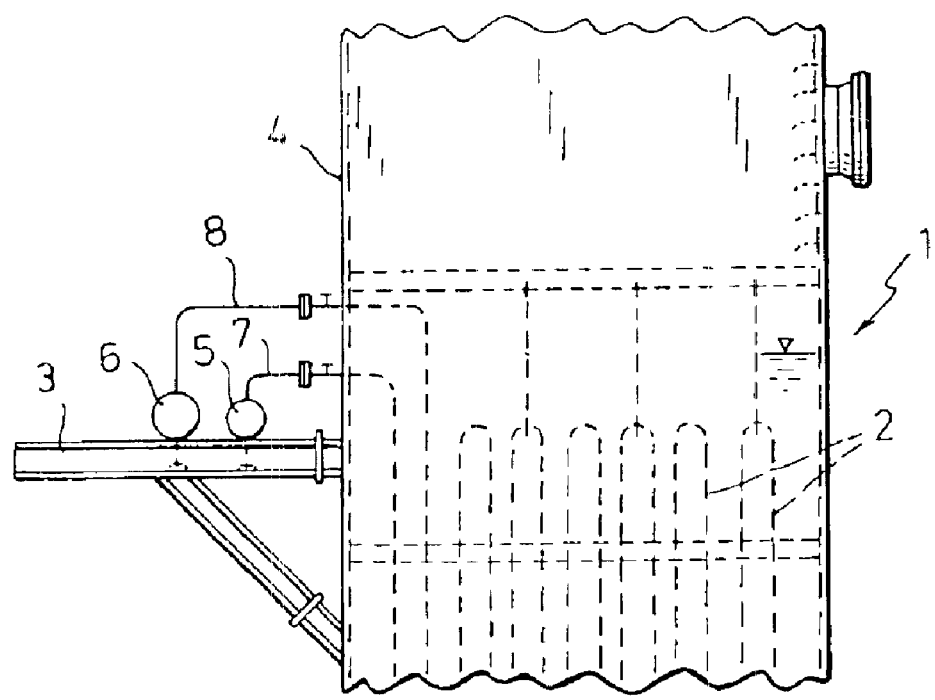

The present invention relates to a fluidized-bed reactor for the oxychlorination of ethylene, oxygen and HCl, comprising a heat exchanger, consisting of a plurality of tube packets, in the fluidized bed for releasing the heat evolved owing to exothermic reactions to a heat-transfer medium in the tube packets, in particular to water/steam, the tube packets coming into contact with water via a ring pipe and the steam being removed via a ring pipe.

In the oxychlorination, ethylene, oxygen and HCl are reacted in a fluidized-bed reactor (oxychlorination reactor) over a copper-containing catalyst to give 1,2-dichloroethane and water. The heat evolved in this reaction is released by the catalyst, via a tube system present in the reactor (and consisting of a plurality of tube packets) to boiler feed water for steam generation or to a heat-transfer medium. The BFW (the heat-transfer medium) is distributed over the tube system to a ring pipe present outside the reactor. The steam formed (the heated-up heat-transfer medium) is collected and removed via a ring pipe, likewise present outside the reactor.

In the known embodiment, there are, inter alia, the following disadvantages: Depending on the number of tube packets in the internal tube system, the two external ring pipes have a large number of connecting pipes through the wall to the tube packets. In the connecting pipes for the cooling water (the heat-transfer medium), aperture plates are used in additional flange connections to achieve uniform distribution over the individual tube packets via the pressure loss. Accessibility and maintenance of the ring pipes are achieved by means of a 360° platform. Simulation of the ring pipes as a model for the pipe stress calculations is very complex and expensive. The oxychlorination reactor must be very carefully insulated to avoid falling below the dew point. Owing to the many wall connection pieces for the ring pipe connections and the platform consoles, this is very difficult and time-consuming.

It is the object of the invention to provide a solution by means of which, while avoiding the disadvantages described above, a compact but economical solution which is easy to manufacture is provided, which solution avoids the expensive drilled holes, and in particular facilitates the calculation of the ring pipes and dispenses with a large number of wall passages.

This object is achieved, according to the invention, by an apparatus of the type defined at the outset if the ring pipe is mounted as a collector or chamber directly on the reactor wall.

By means of the invention, it is possible to replace the large number of wall passages or the aperture plates by simple holes in the internal collector, considerably simplifying the insulation of the reactor.

Further embodiments of the invention are evident from the subclaims, which relate to the particularly expedient designs of the apparatus according to the invention.

In a particular embodiment, for example, the holes for connecting the pipelines are in the form of throttle holes for defining a desired pressure loss and hence for ensuring uniform flows over the various tube packets.

Thus, the pressure distribution in the collector and the pipelines can be influenced by the corresponding precalculated choice of the diameter alone.

The invention is illustrated in more detail below, by way of example, with reference to the drawing. This shows in FIG. 1 a schematic simplified diagram of the passage region of the pipelines according to the prior art with external ring collectors, FIG. 2 by way of comparison a diagram of the embodiment according to the invention and FIG. 3 to 8 different design variants of the invention as simplified sectional diagrams in the region of the reactor wall.

FIG. 1 shows a solution according to the prior art. Here, the reactor denotes in general by 1 has a large number or tube bundles 2 as heat exchanger, comprising ring pipes 5 and 6, arranged on a console 3 outside the reactor wall 4, pipe 5 and withdrawn steam in the ring pipe 6. It is evident, however, that the feed and discharge pipes 7 and 8, respectively, must be led individually through the reactor wall, and the associated computational, design and manufacturing effort is clear.

Figure 2:
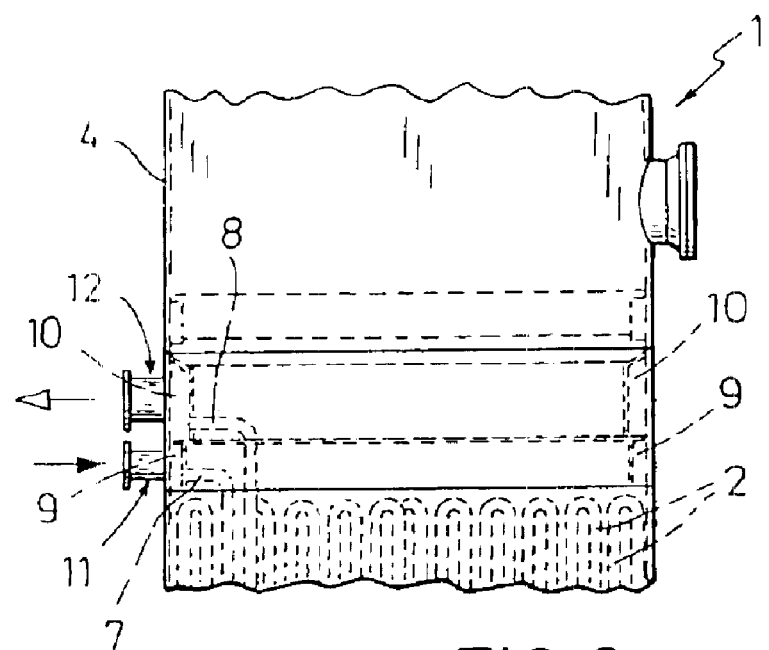
Figure 3:
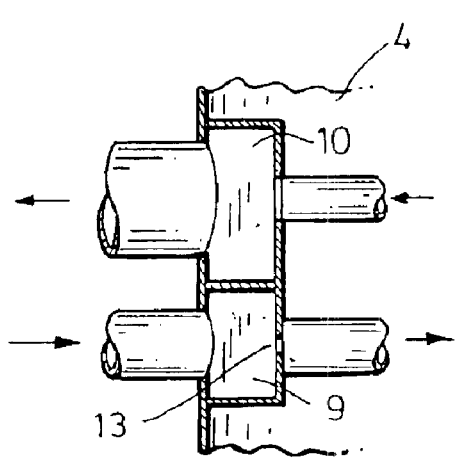
Figure 4:
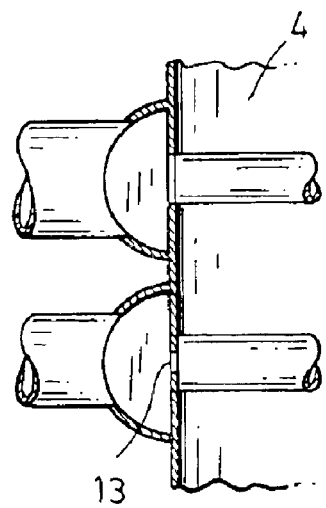
Figure 5:
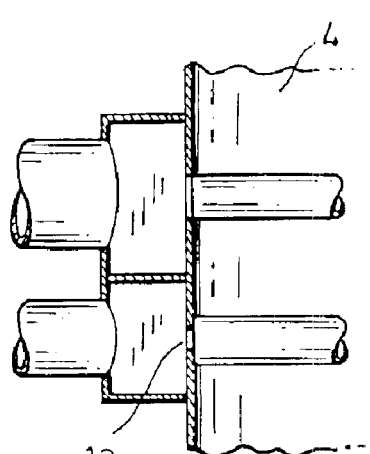
Figure 6:
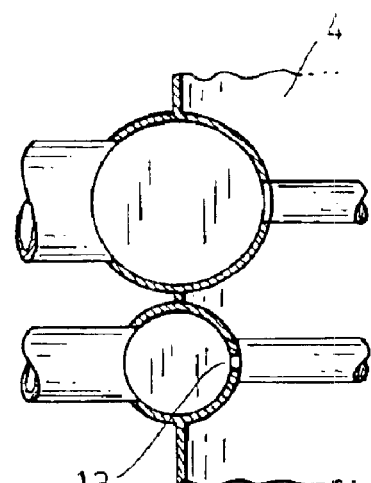
Figure 7:
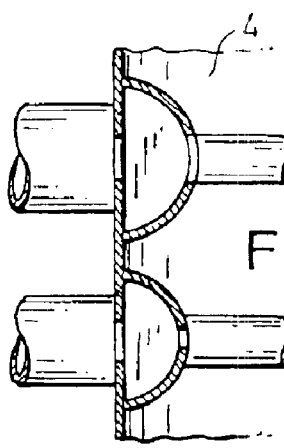
Figure 8:
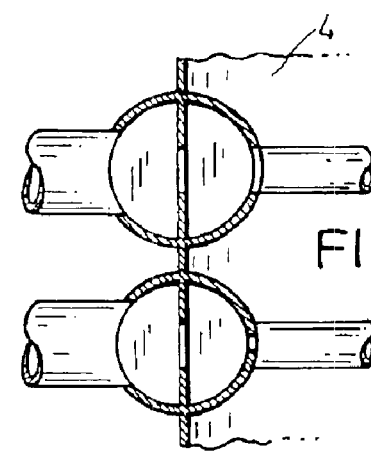

FIG. 2 shows, represented in the same manner, a simplified section through the corresponding part of the reactor according to the invention, likewise denoted by 1. Here, the tube bundles 2 end in two ring collectors 9 and 10 which are mounted in the interior on the wall and are, for example, rectangular or trapezoidal, the heat-exchange medium being introduced via the ring collector or distributor 9 and the steam being removed, for example, via the collector 10. For this purpose, only two transverse connecting pieces 11 and 12 pass through the reactor wall 4, in the example shown in FIG. 2. The feed pipes 7 and the return pipes 8 for the steam pass only through the inner wall of the collectors 9 and 10, respectively.

FIGS. 3 to 8 show embodiments relating to the shape and mounting of the collectors 9 and 10. It is evident that throttle holes, denoted in general by 13, are provided, for example, in the passage walls and also in the reactor wall in order to establish or compensate pressure differences. These holes may vary in size depending on positioning relative to the feed connecting piece and the discharge connecting piece.

What is claimed is:

1. A fluidized-bed reactor for conducting the exothermic reaction of oxychlorination of ethylene, oxygen and HCl, said reactor containing a fluidized bed and having a reactor wall with a heat exchange apparatus, said heat exchange apparatus comprising:

a heat exchanger including a plurality of tube packets positioned in the fluidized bed for releasing heat evolved during the exothermic reaction to a heat-transfer medium comprising water within the tube packets;

a ring pipe distributor coupled to the heat exchanger and mounted to the reactor wall, wherein the ring pipe distributor is essentially circular in cross section and mounted both internal to and external to the reactor wall, with essentially one-half of the cross section assigned to the interior of the reactor wall and essentially one-half of the cross-section assigned to the exterior of the reactor wall; and a ring pipe collector coupled to the heat exchanger and mounted to the reactor wall, wherein the ring pipe collector is essentially circular in cross section and mounted both internal to and external to the reactor wall, with essentially one-half of the cross section assigned to the interior of the reactor wall and essentially one-half of the cross-section assigned to the exterior of the reactor wall;

wherein the water is distributed to the plurality of tube packets via the ring pipe distributor, and wherein the steam generated within the plurality of tube packets is removed from the tube packets via the ring pipe collector; and wherein the ring pipe distributor and the ring pipe collector each include throttle holes located in a position selected from the group consisting of:

the coupling between the ring pipe distributor or collector and the heat exchanger;

the reactor wall between the two-halves of the ring pipe distributor or collector; and both the coupling between the ring pipe distributor or collector and the heat exchanger, and the reactor wall between the two-halves of the ring pipe distributor or collector.

2. The fluidized-bed reactor of claim 1 which includes throttle holes located in both the coupling between the ring pipe distributor or collector and the heat exchanger to define a first opening, and the reactor wall between the two-halves of the ring pipe distributor or collector to define a second opening.

3. A fluidized bed reactor in accordance with claim 2, wherein the first and second openings have the same dimension.

4. A fluidized bed reactor in accordance with claim 2, wherein the first and second openings have different dimensions.

5. A heat exchange apparatus for releasing heat evolved in a fluidized bed reactor from the exothermic reaction of oxychlorination of ethylene, oxygen and HCl, said fluidized bed reactor containing a fluidized bed and having a reactor wall, said heat exchange apparatus comprising:
  plurality of tube packets positioned in the fluidized bed, said plurality of tube packets being pressurized with a heat-transfer medium;
  a ring pipe distributor mounted to the reactor wall and coupled to the plurality of tube packets; and
  a ring pipe collector mounted to the reactor wall and coupled to the plurality of tube packets;
  wherein the plurality of tube packets are pressurized with the heat-transfer medium distributed via the ring pipe distributor, and wherein the heat-transfer medium is removed from the plurality of tube packets via the ring pipe collector;
  wherein the ring pipe distributor is essentially circular in cross section and mounted to the reactor wall both internal to and external to the reactor wall, with essentially one-half of the cross section assigned to the interior of the reactor wall and essentially one-half of the cross section assigned to the exterior of the reactor wall;
  wherein the ring pipe collector is essentially circular in cross section and mounted to the reactor wall both internal to and external to the reactor wall, with essentially one-half of the cross section assigned to the interior of the reactor wall and essentially one-half of the cross section assigned to the exterior of the reactor wall; and
  wherein the ring pipe distributor and the ring pipe collector each include throttle holes located in a position selected from the group consisting of:
  the coupling between the ring pipe distributor or collector and the heat exchanger;
  the reactor wall between the two-halves of the ring pipe distributor or collector; and
  both the coupling between the ring pipe distributor or collector and the heat exchanger, and the reactor wall between the two-halves of the ring pipe distributor or collector.

6. The heat exchange apparatus of claim 5 which includes throttle holes located in both the coupling between the ring pipe distributor or collector and the heat exchanger to define a first opening, and the reactor wall between the two-halves of the ring pipe distributor or collector to define a second opening.

7. A heat exchange apparatus in accordance with claim 6, wherein the first and second openings have the same dimension.

8. A heat exchange apparatus in accordance with claim 6, wherein the first and second openings have different dimensions.

9. A method of providing heat exchange in a fluidized bed reactor for conducting the exothermic reaction of oxychlorination of ethylene, oxygen and HCl, the fluidized bed reactor having a fluidized bed and a reactor wall, the method comprising the steps of:
  providing a heat exchanger including a plurality of tube packets to the fluidized bed reactor, wherein said tube packets are positioned within the fluidized bed for releasing heat evolved from the exothermic reaction to a heat-transfer medium comprising water flowing in the tube packets;
  coupling a ring pipe distributor to the heat exchanger and mounting the ring pipe distributor to the reactor wall both internal to and external to the reactor wall;
  coupling a ring pipe collector to the heat exchanger and mounting the ring pipe collector to the reactor wall both internal to and external to the reactor wall;
  pressurizing the plurality of tube packets with the water distributed via the ring pipe distributor, and
  removing steam generated within the plurality of tube packets via the ring pipe collector;
  wherein the ring pipe distributor is designed to be essentially circular in cross section, with essentially one-half of the cross section assigned to the interior of the reactor wall and essentially one-half of the cross-section assigned to the exterior of the reactor wall, and wherein a first internal distributor opening is defined on the reactor wall between the two-halves of the ring pipe distributor, the first internal distributor opening having an opening dimension less than the diameter of the circular cross-section of the ring pipe distributor;
  wherein the ring pipe collector is designed to be essentially circular in cross section, with essentially one-half of the cross section assigned to the interior of the reactor wall and essentially one-half of the cross section assigned to the exterior of the reactor wall, and wherein a first internal collector opening is defined on the reactor wall between the two-halves of the ring pipe collector, the first internal collector opening having an opening dimension less than the diameter of the circular cross-section of the ring pipe collector;
  wherein the coupling between the ring pipe distributor and the heat exchanger includes a second internal distributor opening therebetween, said first and second internal distributor openings functioning as throttle holes for defining a desired pressure loss and hence for ensuring uniform flow of heat transfer medium in the plurality of tube packets; and
  wherein the coupling between the ring pipe collector and the heat exchanger includes a second internal collector opening therebetween, said first and second internal collector openings functioning as throttle holes for defining a desired pressure loss and hence for ensuring uniform flow of heat transfer medium in the plurality of tube packets.

10. A method in accordance with claim 9, wherein the first and second internal destributor or collector openings have the same dimension.

11. A method in accordance with claim 9, wherein the first and second internal destributor or collector openings have different dimensions.

* * * * *

UNITED STATES PATENT AND TRADEMARK OFFICE
CERTIFICATE OF CORRECTION

PATENT NO. : 6,911,185 B1  Page 1 of 1
APPLICATION NO. : 09/415673
DATED : June 28, 2005
INVENTOR(S) : H. Shon It is certified that error appears in the above-identified patent and that said Letters Patent is hereby corrected as shown below:

Title Page, Item (54) and Col. 1, Lines 1–2, Title should be deleted and substituted with the following:

-- FLUIDIZED-BED REACTOR FOR THE OXYCHLORINATION OF ETHYLENE, OXYGEN AND HCL --

Title Page, Item (75) should be deleted and substituted with the following:

-- (75) Inventor: Hartmut Shon, Oberusel (DE) --

Title Page, Item (73) should be deleted and substituted with the following:

-- (73) Assignee: Uhde GmbH, Dortmund (DE) --

Signed and Sealed this

Twenty-fourth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 6,911,185 B1  Page 1 of 1
APPLICATION NO. : 09/415673
DATED : June 28, 2005
INVENTOR(S) : H. Schon It is certified that error appears in the above-identified patent and that said Letters Patent is hereby corrected as shown below:

Title Page, Item (75) should be deleted and substituted with the following:

-- (75) Inventor: Hartmut Schon, Oberusel (DE) --

Signed and Sealed this

Seventeenth Day of July, 2007

JON W. DUDAS
*Director of the United States Patent and Trademark Office*